(12) United States Patent
Camden

(10) Patent No.: US 6,251,870 B1
(45) Date of Patent: Jun. 26, 2001

(54) PHARMACEUTICAL COMPOSITION FOR INHIBITING GROWTH OF CANCERS

(75) Inventor: James Berger Camden, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/364,021

(22) Filed: Jul. 30, 1999

Related U.S. Application Data

(62) Division of application No. 08/876,705, filed on Jun. 16, 1997, now Pat. No. 5,932,609, which is a division of application No. 08/680,468, filed on Jul. 15, 1996, now Pat. No. 5,932,604.

(51) Int. Cl.[7] .................. A61K 31/70; A61K 31/495; A61K 31/50; A61K 31/505; A61K 31/34; A61K 31/27; A61K 31/135; A61K 31/10
(52) U.S. Cl. .................. 514/43; 514/49; 514/249; 514/274; 514/474; 514/479; 514/648; 514/711
(58) Field of Search .................. 514/474, 479, 514/711, 249, 274, 43, 49, 648

(56) References Cited

U.S. PATENT DOCUMENTS

| | | | |
|---|---|---|---|
| 2,695,225 | 11/1954 | Witman | 71/2.4 |
| 2,734,911 | 2/1956 | Strain | 260/471 |
| 2,806,051 | 9/1957 | Brockway | 260/471 |
| 3,799,758 | 3/1974 | Franz | 71/86 |
| 3,853,530 | 12/1974 | Franz | 71/76 |
| 3,903,297 | 9/1975 | Robert | 424/305 |
| 4,408,052 | 10/1983 | Hozumi | 546/22 |
| 4,542,219 | 9/1985 | Hozumi | 546/22 |
| 4,544,512 | 10/1985 | Hozumi et al. | 260/925 |
| 4,649,203 | 3/1987 | Nojima | 548/112 |
| 4,775,758 | 10/1988 | Nojima | 546/22 |
| 4,866,059 | 9/1989 | Temple | 514/248 |
| 5,114,951 | 5/1992 | King | 514/290 |
| 5,254,715 | 10/1993 | Picard et al. | 560/13 |
| 5,336,690 | 8/1994 | Picard et al. | 514/5 |
| 5,629,341 | 5/1997 | Camden | 514/485 |
| 5,656,615 | 8/1997 | Camden | 514/76 |
| 5,932,604 * | 8/1999 | Camden | 514/394 |
| 5,932,609 * | 8/1999 | Camden | 514/449 |

FOREIGN PATENT DOCUMENTS

| | | |
|---|---|---|
| WO 96/32103 | 10/1996 | (WO) . |
| WO 96/32104 | 10/1996 | (WO) . |

OTHER PUBLICATIONS

Dialog, Elsevier Science Publishers Abst., No. 212600, XP002011351 of Brown et al., J. Cell. Biol., vol. 16, No. 2., 514–536 (1974).
Dus et al. Arch. Immunol. Ther. Exp., vol. 33, No. 219, 325–329 (1985).
Bandruina, et al., Pharm. Chem.J., vol. 12, No. 11, 35–37 (Nov., 1978).
Mochida, et al. Trop. Agric. Res. Ser., vol. 19, 195–208 (1985).
Wattenburg, "Inhibitors of Colon Carcinogenesis" Cancer 40 (5) pp. 2432–2435 (Nov., 1977).
Audus, Herbicides, 2nd ed., vol. 2, pp. 55–82, 385–387 Academic Press (1976).
Schuster " Effects of Herbicides of the Urea and Carbamate Type" Ber. Inst. Tabakforschung Band 20 pp. 25–37 (1973).
NASR, "Computer Assisted Structure–Anticancer Activity" J. Pharm. Sci., 74(8) p 831–836 (Aug., 1985).
Zilkah, "Effect of Inhibitors of Plant Cell Division on Mammalian Tumor Cells," Cancer Research , 41, 1879–1883 (May, 1981).
Zilkah, et al. Proc. Am. Assoc. Cancer Res., vol. 22, 270 (1981).
Merck Index, 11th ed., Merck & Co., Inc. (Rahway, NJ, 1989) p 1232 (#7769).
Pratt, William P, et al., The Anticancer Drugs, 2nd edition, (1994) pp. 86–87, Oxford University Press (New York).

* cited by examiner

Primary Examiner—Jerome D. Goldberg
(74) Attorney, Agent, or Firm—Rose Ann Dabek; Steven W. Miller

(57) ABSTRACT

This invention is a pharmaceutical composition that inhibits the growth of cancers and tumors in mammals, particularly in human and warm blooded animals. The composition contains N-chlorophenylcarbamates and N-chlorophenylthiocarbamates along with a chemotherapeutic agent and optionally a potentiator. A composition for treating viral infections in animals or humans comprising a safe and effective amount of N-chlorophenylcarbamates and the N-chlorophenylthiocarbamates and a potentiator is also disclosed.

17 Claims, No Drawings

PHARMACEUTICAL COMPOSITION FOR INHIBITING GROWTH OF CANCERS

This is a division of application Ser. No. 08/876,705, filed on Jun. 16, 1997 now U.S. Pat. No. 5,932,609 which is a division of Ser. No. 08/680,468 filed on Jul. 15, 1996 now U.S. Pat. No. 5,932,604.

TECHNICAL FIELD

This invention is a pharmaceutical composition that inhibits the growth of cancers and tumors in mammals, particularly in human and warm blooded animals. The composition is also effective against viruses. The composition contains N-chlorophenylcarbamates and N-chlorophenylthiocarbamates along with potentiators or chemotherapeutic agents or antiviral drugs.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable.

Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier, chemotherapy agent and a N-chlorophenylcarbamate or N-chlorophenylthiocarbamate derivative as defined herein, along with a method of treating such cancers.

These compositions are also effective against viruses. Therefore it is a further object of this invention to provide a composition effective against HIV, herpes, influenza, rhinoviruses and the like wherein a potentiator is used to improve the effectiveness of the composition.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount anti-cancer compound selected from the group consisting of N-chlorophenylcarbamates and N-chlorophenylthiocarbamates of the formula:

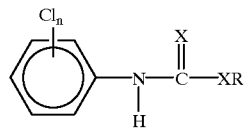

wherein n is from 1 to 3, X is oxygen or sulfur, and R is selected from the group consisting of hydrogen, lower alkyl and lower alkenyl, cyclohexyl, phenalkyl radicals of up to 8 carbon atoms, and phenyl, and pharmaceutically acceptable inorganic or organic acid salts of these compounds.

These compositions can be used to inhibit the growth of cancers and other malignant tumors in humans or animals by administration of an effective amount of the N-chlorophenylcarbamates and N-chlorophenylthiocarbamates either orally, rectally, topically or parenterally, intravenously, or by direct injection near or into the tumor. These compositions are effective in killing or slowing the growth of tumors, yet are safer than adriamycin on normal, healthy cells. The compositions are also useful for treating viral infections.

DETAILED DESCRIPTION OF THE INVENTION

A. Definitions:

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" includes a pharmaceutically acceptable salt of the anti-cancer compound. These include organic or inorganic acid salts of the amines. Preferred acid salts are the hydrochlorides, acetates, salicylates, nitrates and phosphates.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or tumors found in mammals, it includes leukemia.

As used herein, the "anti-cancer compounds" are N-chlorophenylcarbamates and N-chlorophenylthiocarbamates.

As used herein, "viruses" includes viruses which cause diseases (viral infection) in man and other warm blooded animals such as HIV virus, herpes, influenza and rhinoviruses.

As used herein "potentiators" are materials such as triprolidine and its cis-isomer which are used in combination with N-chlorophenylcarbamates and N-chlorophenylthiocarbamates. Potentiators can affect the immune system or enhance the effectiveness of the drugs.

As used herein "chemotherapeutic agents" includes DNA-interactive Agents, Antimetabolites, Tubulin-Interactive Agents, Hormonal agents and others, such as Asparaginase or hydroxyurea.

B. The Anti-Cancer Compounds

The anti-cancer compounds are N-chlorophenylcarbamates and N-chlorophenylthiocarbamates which are known for their herbicidal activities. They are systemic herbicides used to prevent and eradicate certain plants or weeds. Systemic herbicides are differentiated from other herbicides by their ability to be absorbed by the plant and to move through the plant. This systemic ability is not a necessary requirement of the compounds of this invention.

The compounds have the following structure

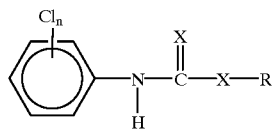

wherein n is from 1 to 3, X is oxygen or sulfur and R is selected from the group consisting of hydrogen, lower alkyl and lower alkenyl, cyclohexyl, phenalkyl of up to 8 carbon atoms and phenyl, and the pharmaceutically acceptable salts of these compounds.

Preferred compounds are those in which R is alkyl with 1 to 4 carbons, preferably, isopropyl and X is oxygen, n is 1 and the chloro group is in the 3 position on the phenyl group. N-3-chlorophenylcarbamate is a most preferred compound.

These compounds are prepared according to the method described in U.S. Pat. No. 2,695,225 issued to Witman (1954) and U.S. Pat. No. 2,734,911 issued to Strain (1956).

C. Chemotherapeutic Agents

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with N-chlorophenylcarbamates and N-chlorophenylthiocarbamates include members of all of these groups. For a detailed discussion of the chemotherapeutic agents and their method of administration, see Dorr, et al, *Cancer Chemotherapy Handbook*, 2d edition, pages 15–34, Appleton & Lange (Connecticut, 1994) herein incorporated by reference.

DNA-interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposde; and the DNA minor groove binder Plcamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimeterxate pyrimidine antagonists; such as Fluorouracil, Fluorodeoxyuridine, CB3717 ($N^{10}$-propargyl-5,8-dideazafolic acid), Azacitidine, Cytarabine, and Floxuridine;

purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol;

androgens such as testosterone, testosterone propionate; fluoxymesterone, methyltestosterone;

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methyiprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamosifen, antiandrogen agents such as Flutamide; and antiadrenal agents such as AMitotane and Aminoglutethimide.

Hydroxyurea appears to act primarily through inhibition of the enzyme ribonucleotide reductase.

Asparaginase is an enzyme which converts asparagine to nonfunctional aspartic acid and thus blocks protein synthesis in the tumor.

Taxol is a preferred chemotherapeutic agent.

D. Potentiators

The "potentiators" can be any material which improves or increase the efficacy of the pharmaceutical composition or acts on the immune system. One such potentiator is triprolidine and its cis-isomer which are used in combination with the chemotherapeutic agents and the N-chlorophenylcarbamates and N-chlorophenylthiocarbamates. Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl) benzimidazole; propazol]. Procodazole is a non-specific active immunoprotective agent against viral and bacterial infections and can be used with the compositions claimed herein. It is effective with the N-chlorophenylcarbamates and the N-chlorophenylthiocarbamates alone in treating cancers, tumors, leukemia and viral infections or combined with chemotherapeutic agents.

Generally an amount effective to enhance the activity of the pharmaceutical composition is used.

Propionic acid and its salts and esters can also be used in combination with the pharmaceutical compositions claimed herein.

Antioxidant vitamins such as vitamins A, C and E and beta-carotene can be added to these compositions.

E. Dosage

Any suitable dosage may be given in the method of the invention. The type of compound and the carrier and the amount will vary widely depending on the species of the warm blooded animal or human, body weight, and tumor being treated. Generally a dosage of between about 2 milligrams (mg) per kilogram (kg) of body weight and about 800 mg per kg of body weight is suitable. Preferably from 15 mg to about 500 mg/kg and most preferably form about 15 mg/kg to about 150 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical or parenteral administration or intravenous administration or by injection into or around the tumor site.

The range and ratio of N-chlorophenylcarbamates and the N-chlorophenylthiocarbamates to chemotherapeutic agent will depend on the type of cancer or tumor being treated and the particular chemotherapeutic agent. The amount of chemotherapeutic agent used can be lower than that of the N-chlorophenylcarbamates and the N-chlorophenylthiocarbamates and can range from 0.5 mg/kg body weight to about 400 mg/kg body weight.

F. Dosage Delivery Forms

The chemotherapeutic agents, N-chlorophenylcarbamates and the N-chlorophenylthiocarbamates and, optionally, the potentiators are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk .powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, ,solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Liebermnan et al., *Pharmaceutical Dosage Forms: Tablets* (1981); and Ansel, *Introduction to Pharmaceutical Dosage Forms 2nd Edition* (1976).

G. Method of Treatment

The method of treatment can be any suitable method which is effective in the treatment of the particular virus or tumor type that is being treated. Treatment may be oral, rectal, topical, parenteral, intravenous administration or injection into or around the tumor site and the like. The method of applying an effective amount also varies depending on the tumor being treated. It is believed that parenteral treatment by intravenous, subcutaneous, or intramuscular application. formulated with an appropriate carrier, additional cancer inhibiting compound or compounds or diluent to facilitate application will be the preferred method of administering the compounds to warm blooded animals.

The method of treating viral infections may also be by oral, rectal, parenteral, topical or intravenous administration. The actual time and dosage will depend on the type of the virus being treated and the desired blood levels.

The following examples are illustrative and are not meant to be limiting to the invention.

In addition to their combination with chemotherapeutic agents and potentiators, N-chlorophenylcarbamates and the N-chlorophenylthiocarbamates can be combined with fungicides, herbicides or other antiviral agents. Preferred herbicides and fungicides include carbendazim, fluoconazole, benomyl, glyphosate and propicodazole.

The N-chlorophenylcarbamates and N-chlorophenylthiocarbamates are also effective against viruses including rhinovirus, HIV, herpes, and influenza.

In the treatment of viral infections, the N-chlorophenylcarbamates and the N-chlorophenylthiocarbamates can be combined with other anti-viral agents to effectively treat viral infections.

HIV Chronic Study

In this model, Chloropropham showed 79% suppression of HIV replication in monocytes. The positive control, interferon, showed 80% suppression. There was 101% increase in HIV replication in T-cells compared to 60% suppression for interferon. AZT showed no action in this model.

Chronic HIV-1 infected cells U1 were derived from an acute HIV-1 infection of the promonocytic cell line, U937. The chronic HIV-1 infected cells, ACH-2 were derived from an acute HIV-1 infection of the T cell line, A3.01.

These cells were cultured in medium and the phorbol ester, PMA. PMA causes the cells (both U1 and ACH-2) to be activated and not divide but it also causes the U-1 cells to differentiate. This results in fewer cells in the PMA-treated cultures than the media alone cultures. Cell viability was measured when these cell lines were treated with the test compounds.

Both cell lines constituitively produce a small amount of HIV-1. ACH-2 cell lines tend to produce more HIV-1 than U1 cells as shown by p-24 ELISA. When either cell line is cultured in the presence of PMA there is an increase in the quantity of HIV-1 produced as measured by the p-24 antigen ELISA.

In addition, the number of institute positive HIV mRNA expressing cells per microscopic field is measured. Comparisons can be made from these numbers since the same number of cells were adhered to the glass slides for each drug concentration ($10 \times 10^6$ cells/ml).

What is claimed is:

1. A pharmaceutical composition for treating cancers or tumors susceptible to treatment comprising:
   a safe and effective amount of a chemotherapeutic agent wherein said chemotherapeutic agent is selected from the group consisting of Methotrexate, Fluorouracil, Fluorodeoxyuridine, $N^{10}$-propargyl-5,8-dideazafolic acid, Azacitidine, Cytarabine, Floxuridine, Mercaptopurine, 6-Thioguanine, Pentostatin, Fludarabine, Tamoxifen and Busulfan; and
   a safe and enhanced amount of an N-chlorophenylcarbamate or N-chlorophenylthiocarbamate of the formula:

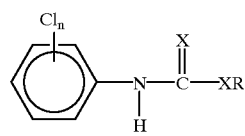

wherein
   n is from 1 to 3;
   X is selected from the group consisting oxygen and sulfur; and
   R is selected from the group consisting of hydrogen, lower alkyl, lower alkenyl, cyclohexyl, phenyl, and phenalkyl of up to 8 carbon atoms;

or a pharmaceutically acceptable inorganic or organic acid salt thereof.

2. A pharmaceutical composition according to claim 1 comprising a pharmaceutically acceptable carrier and a safe and enhanced amount of N-chlorophenylcarbamates and N-chloraphenylthiocarbamates.

3. A pharmaceutical composition according to claim 2 wherein said pharmaceutically acceptable salt is selected from the group consisting of hydrochlorides, acetates, salicylates, nitrates, phosphate salts and mixtures thereof.

4. The pharmaceutical composition of claim 1 wherein the chemotherapeutic agent is Busulfan, and wherein the N-chlorophenylcarbamate is N-3-chlorophenylcarbamate.

5. The pharmaceutical composition of claim 1 wherein the chemotherapeutic agent is Methotrexate, and wherein the N-chlorophenylcarbamate is N-3-chlorophenylcarbamate.

6. The pharmaceutical composition of claim 1 wherein the chemotherapeutic agent is Fluorouracil, and wherein the N-chlorophenylcarbamate is N-3-chlorophenylcarbamate.

7. The pharmaceutical composition of claim 1 wherein the chemotherapeutic agent is azacitidine, and wherein the N-chlorophenylcarbamate is N-3-chlorophenylcarbamate.

8. The pharmaceutical composition of claim 1 wherein the chemotherapeutic agent is cytarabine, and wherein the N-chlorophenylcarbamate is N-3-chlorophenylcarbamate.

9. The pharmaceutical composition of claim 1 wherein the chemotherapeutic agent is pentostatin, and wherein the N-chlorophenylcarbamate is N-3-chlorophenylcarbamate.

10. The pharmaceutical composition of claim 1 wherein the chemotherapeutic agent is tamoxifen, and wherein the N-chlorophenylcarbamate is N-3-chlorophenylcarbamate.

11. A method of treating cancer susceptible to treatment comprising administering a safe and effective amount of a pharmaceutical composition to a patient in need thereof comprising;
    a safe and effective amount of a chemotherapeutic agent wherein said chemotherapeutic agent is selected from the group consisting of Methotrexate, Fluorouracil, Fluorodeoxyuridine, $N^{10}$-propargyl-5,8-dideazafolic acid, Azacitidine, Cytarabine, Floxuridine, Mercaptopurine, 6-Thioguanine, Pentostatin, Fludarabine, Tamoxifen and Busulfan; and
    a safe and enhanced amount of an N-chlorophenylcarbamate or N-chlorophenylthiocarbamate of the formula:

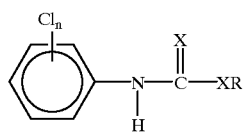

wherein
    n is from 1 to 3,
    X is selected from the group consisting of oxygen and sulfur, and
    R is selected from the group consisting of hydrogen, lower alkyl, lower alkenyl, cyclohexyl, phenalkyl of up to 8 carbon atom, and phenyl,
or a pharmaceutically acceptable organic or inorganic acid salt thereof.

12. The method of claim 11 wherein the chemotherapeutic agent is Busulfan, and wherein the N-chlorophenylcarbamate is N-3-chlorophenylcarbamate.

13. A method of treating cancer according to claim 11 comprising administering a safe and effective amount of an N-chlorophenylcarbamate wherein R is alkyl of from 1 to 4 carbons, n is 1, X is oxygen and the chloro is in the 3 position of the phenyl.

14. A method according to claim 13 wherein from 2 mg/kg body weight to 400 mg/kg of said N-chlorophenylcarbamate is administered.

15. A method according to claim 14 wherein said pharmaceutical composition is administered orally or enterically, intravenously, parenterally or by injection into or around the cancer.

16. A method according to claim 15 wherein from 0.5 mg/kg body weight to 400 mg/kg body weight of said chemotherapeutic agent is administered.

17. A composition effective for treating cancers or tumors susceptible to treatment comprising:
  a safe and effective amount of a chemotherapeutic agent wherein said chemotherapeutic agent is a DNA-interactive Agent; and
  a safe and enhanced amount of an N-chlorophenylcarbamate or N-chlorophenylthiocarbamate of the formula:

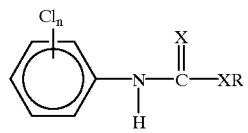

wherein
  X is selected from the group consisting of oxygen and sulfur,
  n is from 1 to 3, and
  R is selected from the group consisting of hydrogen, lower alkyl, lower alkenyl, cyclohexyl, phenalkyl of up to 8 carbon atoms, and phenyl,
  or a pharmaceutically acceptable organic or inorganic acid salt thereof,
and a safe and effective carrier.

* * * * *

UNITED STATES PATENT AND TRADEMARK OFFICE
CERTIFICATE OF CORRECTION

PATENT NO. : 6,251,870 B1  Page 1 of 1
DATED : June 26, 2001
INVENTOR(S) : James Berger Camden It is certified that error appears in the above-identified patent and that said Letters Patent is hereby corrected as shown below:

Title page,
Insert after Item [62], -- [60] Provisional Application No. 60/001,888, Aug. 4, 1995 --.
Item [62], after "5,932,604," insert -- which is a continuation-in-part of 08/420,913, filed on April 12, 1995, now Pat. No. 5,629,341. --

Column 1,
Line 7, after "5,932,604," insert -- which is a continuation-in-part of 08/420,913, filed on April 12, 1995, now Pat. No. 5,629,341. USSN 08/680,468 claims benefit of USSN 60/001,888 filed Aug. 4, 1995. --

Column 7,
Line 50, insert -- effective -- immediately after "enhanced".

Column 8,
Line 5, insert -- effective -- immediately after "enhanced".
Line 6, delete "N-chloraphenylthiocarbamates" and insert therefor, -- N-chlorophenylthiocarbamates --.
Line 43, insert -- effective -- immediately after "enhanced".

Column 9,
Line 19, insert -- effective -- immediately after "enhanced".

Signed and Sealed this

Twenty-first Day of January, 2003

JAMES E. ROGAN
*Director of the United States Patent and Trademark Office*